(12) United States Patent
Auguste et al.

(10) Patent No.: US 7,138,110 B2
(45) Date of Patent: *Nov. 21, 2006

(54) MASCARA COMPRISING SOLID PARTICLES

(75) Inventors: Frederic Auguste, Chevilly-Larue (FR); Florence Tournilhac, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/195,428

(22) Filed: Jul. 16, 2002

(65) Prior Publication Data

US 2003/0059390 A1 Mar. 27, 2003

Related U.S. Application Data

(60) Provisional application No. 60/306,445, filed on Jul. 20, 2001.

(30) Foreign Application Priority Data

Jul. 16, 2001 (FR) .................................. 01 09503

(51) Int. Cl.
  A61Q 1/10 (2006.01)
  A61Q 5/00 (2006.01)
(52) U.S. Cl. ................ 424/70.7; 424/70.1; 424/70.22; 424/70.13; 424/70.16; 424/401
(58) Field of Classification Search ................ 424/401, 424/70.7
See application file for complete search history.

(56) References Cited

U.S. PATENT DOCUMENTS

| | | |
|---|---|---|
| 3,937,811 A | 2/1976 | Papantoniou et al. |
| 5,660,818 A | 8/1997 | Dubief et al. |
| 5,720,943 A | 2/1998 | Mougin et al. |
| 5,849,278 A | 12/1998 | Piot et al. |
| 5,851,517 A | 12/1998 | Mougin et al. |
| 5,858,338 A | 1/1999 | Piot et al. |
| 5,945,095 A | 8/1999 | Mougin et al. |
| 5,961,989 A | 10/1999 | Mougin et al. |
| 6,001,168 A | 12/1999 | Hall-Goulle et al. |
| 6,254,877 B1 | 7/2001 | De La Poterie et al. |
| 6,264,933 B1 | 7/2001 | Bodelin et al. |
| 6,274,131 B1 | 8/2001 | Piot et al. |
| 6,372,201 B1 | 4/2002 | Leuridan et al. |
| 2001/0006665 A1 | 7/2001 | Auguste |
| 2002/0085986 A1 | 7/2002 | De La Poterie et al. |

FOREIGN PATENT DOCUMENTS

| EP | 0 557 196 | 8/1993 |
|---|---|---|
| EP | 0 749 746 | 12/1996 |
| EP | 0 749 747 | 12/1996 |
| EP | 0 764 436 | 3/1997 |
| EP | 0 930 060 | 7/1999 |
| EP | 1 040 814 | 10/2000 |
| EP | 1 048 282 | 11/2000 |
| EP | 1 064 924 | 1/2001 |
| EP | 1 108 415 | 6/2001 |
| EP | 1 201 222 | 5/2002 |
| FR | 2 232 303 | 1/1975 |
| FR | 2 687 569 | 8/1993 |
| FR | 2 718 455 | 10/1995 |
| FR | 2 719 468 | 11/1995 |
| FR | 2 756 731 | 6/1998 |
| FR | 2 773 063 | 7/1999 |
| FR | 2 787 318 | 6/2000 |
| FR | 2 792 190 | 10/2000 |
| FR | 2 801 501 | 6/2001 |
| JP | H04-210613 | 7/1992 |
| JP | H06-9341 | 1/1994 |
| JP | H07-291823 | 11/1995 |
| JP | H07-304639 | 11/1995 |
| JP | H09-2920 | 1/1997 |
| JP | H09-110631 | 4/1997 |
| JP | H09-202714 | 8/1997 |
| JP | H10-175845 | 6/1998 |
| JP | H11-255619 | 9/1999 |
| JP | 2000-191444 | 7/2000 |
| JP | 2001-31526 | 2/2001 |
| JP | 2001-192559 | 7/2001 |
| WO | WO 98/23251 | 6/1998 |

OTHER PUBLICATIONS

Kirk-Othmer, "Encyclopedia of Chemical Technology," Third Edition, vol. 22, John Wiley & Sons, 1983, pp. 333-433.
English language Derwent Abstract of EP 0 847 752, Jun. 17, 1998.
English language Derwent Abstract of EP 0 923 928, Jun. 23, 1999.
English language Derwent Abstract of EP 1 048 282, Nov. 2, 2000.
English language Derwent Abstract of EP 1 064 920, Jan. 3, 2001.
English language Derwent Abstract of EP 1 082 953, Mar. 14, 2001.
English language Derwent Abstract of FR 2 792 190, Oct. 20, 2000.
English language Derwent Abstract of FR 2 794 970, Dec. 22, 2000.
Office Action in co-pending U.S. Appl. No. 10/195,430, dated Aug. 5, 2005 (Ex. J. Venkat).

(Continued)

Primary Examiner—Jyothsna Venkat
(74) Attorney, Agent, or Firm—Finnegan, Henderson, Farabow, Garrett & Dunner, L.L.P.

(57) ABSTRACT

A composition for coating keratinous fibers comprising, in a cosmetically acceptable medium, at least one volatile solvent and a nonvolatile fraction comprising:
  at least one polymer capable of adhering to the keratinous fibers,
  first solid particles comprising a first at least one amorphous material which is solid at 25° C. exhibiting a glass transition (Tg) greater than or equal to 60° C., the first solid particles being present in the composition in an amount such that the volume fraction of the first solid particles is greater than or equal to 50% of the total volume of the nonvolatile fraction of the composition.

The composition makes it possible to obtain good curling of keratinous fibers, such as eyelashes.

90 Claims, No Drawings

OTHER PUBLICATIONS

Office Action in co-pending U.S. Appl. No. 10/195,432, dated Dec. 2, 2003 (Ex. J. Venkat).

Office Action in co-pending U.S. Appl. No. 10/195,432, dated Jun. 10, 2004 (Ex. J. Venkat).

Office Action in co-pending U.S. Appl. No. 10/195,432, dated Mar. 25, 2005 (Ex. J. Venkat).

Notice of Allowance in co-pending U.S. Appl. No. 10/195,419, dated Nov. 14, 2005 (Ex. J. Venkat).

French Search Report for FR 01 09504 dated May 27, 2002 (Priority Application for co-pending U.S. Appl. No. 10/195,432; Examiner D. Willekens.

English language JPO Abstract for JP-H09-2920.

English language JPO Abstract for JP-H10-175845.

English language Derwent Abstract for JP-H09-202714.

English language Derwent Abstract for JP-2001-31526.

Office Action in co-pending U.S. Appl. No. 10/195,430, dated Nov. 26, 2003 (Ex. J. Venkat).

Office Action in co-pending U.S. Appl. No. 10/195,430, dated May 19, 2004 (Ex. J. Venkat).

Office Action in co-pending U.S. Appl. No. 10/195,430, dated Nov. 22, 2004 (Ex. J. Venkat).

Office Action in co-pending U.S. Appl. No. 10/195,419, dated Dec. 3, 2003 (Ex. J. Venkat).

Office Action in co-pending U.S. Appl. No. 10/195,419, dated Jun. 3, 2004 (Ex. J. Venkat).

Office Action in co-pending U.S. Appl. No. 10/195,419, dated Mar. 25, 2005 (Ex. J. Venkat).

French Search Report for FR 01 09502 dated Apr. 22, 2002, Examiner D. Angiolini.

French Search Reportfor FR 01 09505 dated May 27, 2002, Examiner G. Willekens.

English language Derwent Abstract for EP 1 048 282.

English language Derwent Abstract for EP 1 064 924.

MASCARA COMPRISING SOLID PARTICLES

This application claims priority of U.S. Provisional Application No. 60/306,445, filed Jul. 20, 2001.

The subject of the present invention is a cosmetic composition for coating keratinous fibres, such as eyelashes or hair, comprising solid particles and an adherent polymer, and its use for curling keratinous fibres. The composition can be used on substantially longitudinal keratinous fibres of humans such as eyelashes or hair or alternatively false eyelashes or pastiches such as wigs. For instance, the composition is intended for coating the eyelashes.

The composition may be a make-up composition, also called mascara, a composition to be applied over a make up, also called top coat, or alternatively a composition for treating keratinous fibres, such as eyelashes. For instance, the composition can be a mascara.

An aim of the present invention is to provide a composition for coating eyelashes leading, after application, to a coat conferring good curling of the eyelashes.

The inventors have discovered that such a coating of the eyelashes could be obtained using particular solid particles combined with an adherent polymer.

More precisely, the subject of the invention is a composition for coating keratinous fibres comprising, in a cosmetically acceptable medium comprising at least one volatile solvent, a nonvolatile fraction comprising:

at least one polymer capable of adhering to the keratinous fibres, first solid particles comprising a first at least one amorphous material which is solid at 25° C. exhibiting a glass transition (Tg) greater than or equal to 60° C., and optionally second solid particles comprising a second material different from the first material, the second solid particles not being capable of coalescing at a temperature of less than 40° C., the first and, where appropriate, the second solid particles being present in the composition in an amount such that the volume fraction of the first solid particles and, where appropriate, of the second solid particles is greater than or equal to 50% of the total volume of the nonvolatile fraction of the composition.

The subject of the invention is also a method for applying make-up to or the nontherapeutic treatment of keratinous fibres, such as eyelashes, comprising the application to keratinous fibres of a composition as defined above.

The subject of the invention is also the use of a composition as defined above for curling keratinous fibres, such as eyelashes.

The subject of the invention is also the use of first solid particles of a first at least one amorphous material which is solid at 25° C. having a glass transition temperature greater than 60° C., and optionally of second solid particles of a second material different from the first material, the second solid particles not being capable of coalescing at a temperature of less than or equal to 40° C., in a composition for coating keratinous fibres, such as a mascara, comprising, in a cosmetically acceptable medium comprising at least one volatile solvent, a nonvolatile fraction comprising at least one polymer capable of adhering to the keratinous fibers and comprising the said first and, optionally, second solid particles, the first solid particles and, where appropriate, the second solid particles being present in the composition in an amount such that the volume fraction of the first solid particles and, where appropriate, of the second solid particles is greater than or equal 50% of the total volume of the nonvolatile fraction of the composition, for curling keratinous fibres, such as eyelashes.

The expression solid particles is understood to mean particles which are in the solid state at 25° C. and at atmospheric pressure.

The expression nonvolatile fraction of the composition is defined herein to mean the combination of the constituents present in the composition which are not volatile. The expression volatile compound is defined herein to mean a compound which, taken in isolation, has a non-zero vapour pressure, at room temperature (25° C.) and atmospheric pressure, such as ranging from $10^{-2}$ to 300 mmHg (1.33 Pa to 40 000 Pa) and further such as greater than 0.3 mmHg (40 Pa).

The nonvolatile fraction of the composition in fact corresponds to the mixture of the constituents remaining on the eyelashes after drying of the mascara applied to the eyelashes.

To obtain good curling of the eyelashes, the composition according to the invention comprises solid particles, called first solid particles, comprising, such as or formed of, at least one amorphous material, called first at least one amorphous material, having a glass transition temperature greater than or equal to 60° C. (such as ranging from 60° C. to 800° C.), further such as greater than or equal to 80° C. (such as ranging from 80° C. to 700° C.), and even further such as greater than or equal to 100° C. (such as ranging from 100° C. to 500° C.). The glass transition temperature may be measured by DSC (Differential Scanning Calorimetry) according to the ASTM D3418-97 standard.

A representative amorphous material that may be used is a polymer which is nonfilm-forming at a temperature of less than or equal to 40° C. and which has a glass transition temperature as described above.

The expression "nonfilm-forming polymer at a temperature of less than 40° C." is defined herein to mean a polymer which is not capable of forming, on its own or in the presence of a film-forming aid, a continuous film which is adherent to a support, such as to keratinous fibers, at a temperature of less than or equal to 40° C.

The expression film-forming aid is defined herein to mean plasticizing agents and coalescing agents known to persons skilled in the art for promoting film formation by polymers.

As amorphous polymer having a glass transition temperature of greater than or equal to 60° C., there may be used free-radical polymers or polycondensates having this defined glass transition temperature.

As free-radical polymer, there may be mentioned:

polymers of ethylene, for example of cycloethylene, and of naphthylethylene;

polymers of propylene, for example of hexafluoropropylene;

acrylic polymers, such as polymers of acrylic acid, of dimethyl-adamanthyl acrylate, and of chloroacrylate;

polymers of acrylamide;

polymers of (meth)acrylonitrile;

polymers of acetylstyrene, of carboxystyrene, and of chloromethylstyrene.

As polycondensates, there may be mentioned polycarbonates, polyurethanes, polyesters, polyamides, polysulphones, polysulphonamides and carbohydrates such as amylose triacetate.

The first solid particles may be solid particles or hollow particles.

According to one embodiment, the first solid particles are essentially formed of the said at least one amorphous material described above.

According to another embodiment, the first solid particles comprise at least the said first amorphous material and at least one additional material, different from the first amorphous material, the said first amorphous material forming the surface, or the crust, of the said first solid particles and the additional material forming the inside, or the core, of the said first solid particles.

The additional material may be, for example, an additional polymer having a glass transition temperature of less than 60° C., for instance less than 45° C.

Thus, the first solid particles may be, for example, core-shell particles of polymers comprising an outer part (that is to say a crust) formed of the first amorphous material having a glass transition temperature of greater than or equal to 60° C. and comprising an inner part (that is to say a core) having a glass transition temperature of less than 60° C.

In an embodiment of the invention, the content of the first amorphous material in the first solid particles is such that the volume fraction of the first material is greater than or equal to 10%, such as greater than or equal to 30%, by volume of the total volume of the first solid particles.

The first solid particles may have a mean size ranging from 10 nm to 50 µm, such as ranging from 20 nm to 1 µm, as measured by methods known to those skilled in the art.

As first solid particles, there may be used aqueous dispersions of nonfilm-forming polymer which are sold under the names "JONCRYL® SCX 8082", "JONCRYL® 90" by the company JOHNSON POLYMER, "NEOCRYL® XK 52" by the company AVECIA RESINS and "RHODOPAS® 5051" by the company RHODIA CHIMIE.

The composition according to the invention may comprise, in addition to the first solid particles described above, other solid particles, called second particles, different from the first solid particles.

These second solid particles correspond to the particles which are solid at 25° C. of any material, different from the first solid particles, remaining in the form of individualized solid particles, or optionally of particles stuck together but which retain, in this case, their individual particle state (these solid particles stuck together are not coalesced at a temperature of less than or equal to 40° C.).

For instance, the second solid particles may comprise:
solid particles, called second primary solid particles, comprising, such as formed of, at least one material chosen from crystalline and semicrystalline materials having a glass transition temperature of greater than or equal to 60° C.,
and/or solid particles, called second secondary solid particles, comprising, such as formed of, a wax having a hardness of greater than 6.5 MPa,
and/or other solid particles, called second tertiary solid particles, different from the said second primary and secondary solid particles,
and mixtures thereof.

The second primary solid particles are solid particles comprising, such as formed of, at least one material, called first material, chosen from crystalline and semicrystalline materials which are solid at room temperature (25° C.) and have at least one of a first order phase transition, a melting transition, and a combustion transition, greater than 100° C., such as greater than 120° C., and further such as greater than 150° C.

The melting or combustion temperature of the first material may be measured according to the ASTM E794-98 standard.

The expression "semicrystalline material" is defined herein to mean within the context of the invention, a material, such as a polymer, comprising a crystallizable part and an amorphous part exhibiting a reversible first order phase transition temperature, such as melting point (solid-liquid transition).

In an embodiment of the invention the first material of the said solid particles exhibits a Vickers hardness greater than or equal to 10, for instance ranging from 10 to 7,500, such as greater than or equal to 200, for instance ranging from 200 to 7,500, and further such as greater than or equal to 400, such as ranging from 400 to 7500.

The VICKERS hardness (HV) is determined by applying to the material a penetrometer in the form of a square-base pyramid, using a load P. The mean size of a diagonal of the square impression obtained with the penetrometer is then measured.

The VICKERS hardness (HV) is then calculated by the relationship:

$$HV = \frac{1854.4 \times P}{d^2} \quad \begin{array}{l} d = \text{mean diagonal in µm} \\ P = \text{load applied in g} \end{array}$$

The measurement of the VICKERS hardness may be carried out using the microdurometer M 400 g 2 from the company LECO.

The first material of the said second primary solid particles may be an inorganic material which may be chosen from silica, glass, diamond, copper, boron nitride, ceramics, micas, metal oxides, such as iron oxides such as black iron oxide, red iron oxide, and yellow iron oxide, titanium oxides, alumina, polyamides such as nylon, and mixtures thereof.

The second primary solid particles may be solid particles, or alternatively hollow particles. For example, there may be used the hollow silica sold under the name "SUNSIL-130" by the company SUNJIN CHEMICAL.

According to an embodiment of the composition according to the invention, the said second primary solid particles are essentially formed of the said first material defined above.

According to another embodiment of the composition according to the invention, the said second primary solid particles comprise, or are even formed essentially of, at least two different first materials. This is, for example, the case of micas coated with titanium oxide or with iron oxide.

According to yet another embodiment of the composition according to the invention, the said second primary solid particles comprise at least the said first material, and at least an additional material, different from the said first material, the said first material forming the surface of the said first solid particles. For these solid particles, the said first material having the characteristics described above, exists at the surface of the said second primary solid particles, the latter comprising an additional material coated with the first material.

For example, the said second primary solid particles may have a mean size ranging from 5 nm to 50 µm, such as from 20 nm to 50 µm, as measured by methods known to those skilled in the art.

The second solid particles may comprise second secondary solid particles comprising at least one wax having a hardness greater than or equal to 6.5 MPa.

The expression "wax" is defined herein to mean, within the context of the present invention, a lipophilic fatty compound, which is solid at room temperature (25° C.) and atmospheric pressure (760 mmHg, that is $10^5$ Pa), with a reversible solid/liquid change of state, having a melting point ranging from 30° C. to 99° C., such as ranging from 45° C. to 99° C.

By heating the wax to its melting point, it is possible to make it miscible with oils and to form a microscopically homogeneous mixture, but on bringing the temperature of the mixture back to room temperature, recrystallization of the wax in the oils of the mixture is obtained.

The melting point values correspond, according to the invention, to the peak of melting measured using a differential scanning calorimeter (DSC), for example the calorimeter sold under the name DSC 30 by the company METLER, with a rise in temperature of 5 or 10° C. per minute.

The hard wax may have a melting point ranging from 30° C. to 99° C., for example ranging from 40° C. to 99° C.

For instance, the hard wax has a melting point greater than or equal to 30° C. and less than 77° C., such as greater than or equal to 30° C. and less than 60° C., further such as ranging from 30° C. to 59° C., even further such as ranging from 35° C. to 59° C., such as ranging from 40° C. to 50° C.

For example, the wax may have a hardness ranging from 6.5 MPa to 20 MPa, such as ranging from 9.7 MPa to 20 MPa, and further such as ranging from 9.7 MPa to 15 MPa. For example, the wax may have a hardness greater than 10 MPa, such as ranging from 10 to 20 MPa, and further such as ranging from 10 to 12 MPa.

According to the present application, the hardness of the wax is determined by measuring the compression force measured at 20° C. using a texturometer sold under the name TA-XT2i by the company RHEO, equipped with a stainless steel cylinder having a diameter of 2 mm, moving at the measuring speed of 0.1 mm/s, and penetrating into the wax at a penetration depth of 0.3 mm. To measure the hardness, the wax is melted at a temperature equal to the melting point of the wax +20° C. The molten wax is poured into a container having a diameter of 30 mm and a depth of 20 mm. The wax is recrystallized at room temperature (25° C.) for 24 hours, and then the wax is stored for at least 1 hour at 20° C. before carrying out the measurement of hardness. The value of the hardness is the measured compacting force divided by the surface area of the texturometer cylinder in contact with the wax.

As wax satisfying the criteria defined above, there may be used Candelilla wax, hydrogenated jojoba wax, sumac wax, ceresin, octacosanyl stearate, tetracontanyl stearate, Shellac wax, behenyl fumarate, di(1,1,1-trimethylolpropane) tetrastearate sold under the name "HEST 2T-4S" by the company HETERENE, di(1,1,1-trimethylolpropane) tetrabehenate sold under the name HEST 2T-4B by the company HETERENE, and ozokerites such as that sold under the name "OZOKERITE WAX SP 1020 P" by the company STRAHL & PITSCH.

It is also possible to use the wax obtained by hydrogenation of olive oil esterified with stearyl alcohol, sold under the name "PHYTOWAX Olive 18 L 57" or alternatively the waxes obtained by hydrogenation of castor oil esterified with cetyl alcohol, sold under the name "PHYTOWAX ricin 16L64 and 22L73" by the company SOPHIM. Such waxes are described in application FR-A-2792190.

For example, the hard wax can be chosen from the olive wax obtained by hydrogenation of olive oil esterified with stearyl alcohol, sold under the name PHYTOWAX Olive 18 L 57 by the company SOPHIM and di(1,1,1-trimethylolpropane) tetrastearate.

For example, the said first particles of hard wax may have a mean size ranging from 50 nm to 50 µm, such as ranging from 50 nm to 10 µm, as measured by methods known to those skilled in the art.

All the constituents present in the composition according to the invention existing in the state of solid particles at 25° C. and which do not coalesce at a temperature of less than or equal to 40° C., on their own or in the presence of the other constituents present in the composition, are considered as being either first solid particles or second solid particles according to the definitions described above.

Thus, for example, the second tertiary particles may be made of a material chosen from waxes, fillers, polymers different from the amorphous material present in the primary and secondary solid particles described above.

The additives described below, when they are in the form of solid particles at 25° C., are considered as being either first solid particles or second solid particles as described above when these additives possess the corresponding characteristics defined above.

For example, the adherent polymer present in the composition according to the invention may be in the form of solid particles. In such case, these particles are considered as being solid particles as defined above if this polymer possesses the characteristics defined above.

In the composition according to the invention, the first solid particles and, where appropriate, the second solid particles are present in an amount such that the volume fraction of the first solid particles and, where appropriate, of the second solid particles is greater than or equal to 50% of the total volume of the nonvolatile fraction of the composition, which means that the total volume of all the first particles and, where appropriate, of the second particles represents at least 50% (such as ranges from 50% to 99%) of the total volume of the nonvolatile fraction of the composition.

The expression "volume fraction of the first solid particles and, where appropriate, of the second solid particles" is defined to mean the percentage total volume of all the first solid particles and, where appropriate, of all the second solid particles present in the nonvolatile fraction of the composition, relative to the total volume of all the compounds of the nonvolatile fraction of the composition.

In an embodiment of the invention, the said volume fraction of the first solid particles and, where appropriate, of the second solid particles is greater than or equal to 60% (such as ranges from 60% to 99%), or further still is greater than or equal to 70% (such as ranges from 70% to 95%) of the total volume of the nonvolatile fraction of the composition.

The volume fraction (VF) of solid particles present in the nonvolatile fraction of the composition is equal to the percentage total volume V of the said particles divided by the total volume V' of the nonvolatile fraction of the composition.

The volume V of solid particles is equal to the mass m of the said solid particles in the composition divided by the density d of the particles. The density is calculated according to the method described below.

Volume fraction: $VF=100 \times V/V'$ and $V=m/d$

The total volume V' of the nonvolatile fraction of the composition is calculated by adding the volume of each nonvolatile constituent present in the composition.

In an embodiment of the invention, when the composition comprises second particles as defined above, the first particles may be present in the composition in an amount such that the volume fraction of the first solid particles is greater than or equal to 10% of the total volume fraction of the first and second solid particles, such as ranging from 10% to 100%, further such as greater than or equal to 20%, even further such as ranging from 20% to 100%, still even further greater than or equal to 30%, such as ranging from 30% to 100%, yet even further greater than or equal to 40%, such as ranging from 40% to 100%, and even further greater than or equal to 50%, such as ranging from 50% to 100%.

For example, when the composition comprises second primary and/or primary solid particles as defined above, the volume fraction of the said first solid particles and of the said second primary and/or secondary solid particles may be greater than or equal to 10.05% (such as ranging from 10.05% to 100%) of the total volume of the first and second solid particles, further such as greater than or equal to 20.05% (such as ranging from 20.05% to 100%), still further greater than or equal to 30.05% (such as ranging from 30.05% to 100%), still even further greater than or equal to 40.05% (such as ranging from 40.05 to 100%), and finally even further greater than or equal to 50.05% (such as ranging from 50.05% to 100%).

The volatile solvent present in the composition according to the invention may be chosen from water, the volatile organic solvents and the volatile oils defined below.

In the present application, the expression "polymer capable of adhering to the keratinous fibers", called later adherent polymer, is defined herein to mean a polymer capable of resting attached to keratinous fibres such as the eyelashes, the hair or the skin, during contact of the polymer with the said keratinous fibers. Such an adherent polymer in fact has a good capacity to form a deposit on the keratinous fibers and remains attached to the latter for a normal period of wear.

For example, the adherent polymer may be a film-forming polymer at a temperature of less than or equal to 40° C. In the present application, the expression "film-forming polymer" is defined herein to mean a polymer capable of forming, on its own or in the presence of a film-forming aid, a continuous deposit, such as a film, which adheres to a support, such as to keratinous fibers.

The adherent polymer present in the composition according to the invention may be a polymer solubilized or dispersed in the form of solid particles in an aqueous phase of the composition or alternatively solubilized or dispersed in the form of solid particles in a liquid fatty phase. The composition may comprise a mixture of these polymers. When the adherent polymer exists in the form of solid particles, these particles may have a mean particle size ranging from 5 nm to 10 µm, such as ranging from 5 nm to 5 µm, further such as ranging from 5 nm to 600 nm, and even further such as ranging from 20 nm to 300 nm, as measured by methods known to those skilled in the art.

The adherent polymer may be present in the composition according to the invention in a dry matter content ranging from 0.1% to 50% by weight relative to the total weight of the composition, such as from 0.5% to 40% by weight, and further such as from 1% to 30% by weight.

Among the adherent polymers which can be used in the composition of the present invention, there may be mentioned synthetic polymers of the free-radical type or of the polycondensate type, polymers of natural origin and mixtures thereof.

The expression free-radical polymer is defined herein to mean a polymer obtained by polymerization of monomers with ethylenic unsaturation for example, each monomer being capable of homopolymerizing (in contrast to polycondensates).

The polymers of the free-radical type may be, for example, chosen from vinyl polymers, copolymers and acrylic polymers.

The vinyl polymers may result from the polymerization of ethylenically unsaturated monomers having at least one acid group and/or esters of these acid monomers and/or amides of these acid monomers.

As a monomer carrying an acid group, there may be used α,β-ethylenic unsaturated carboxylic acids such as acrylic acid, methacrylic acid, crotonic acid, maleic acid, or itaconic acid.

The esters of acid monomers can be chosen from the esters of (meth)acrylic acid (also called (meth)acrylates), such as alkyl, such as $C_1$–$C_{30}$, further such as $C_1$–$C_{20}$, alkyl, (meth)acrylates, aryl, such as $C_6$–$C_{10}$ aryl, (meth)acrylates, hydroxyalkyl, such as $C_2$–$C_6$ hydroxyalkyl, (meth)acrylates.

Among the alkyl (meth)acrylates, there may be mentioned methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates, there may be mentioned hydroxyethyl acrylate, 2-hydroxypropyl acrylate, hydroxyethyl methacrylate and 2-hydroxypropyl methacrylate.

Among the aryl (meth)acrylates, there may be mentioned benzyl acrylate and phenyl acrylate.

The esters of (meth)acrylic acid which can be used are the alkyl (meth)acrylates.

According to the present invention, the alkyl group of the esters may be either fluorinated or perfluorinated, that is to say that some or all of the hydrogen atoms of the alkyl group are substituted with fluorine atoms.

As amides of the acid monomers, there may be mentioned for example (meth)acrylamides, such as N-alkyl(meth)acrylamides, such as of a $C_2$–$C_{12}$ alkyl. Among the N-alkyl (meth)acrylamides, there may be mentioned N-ethylacrylamide, N-t-butylacrylamide, N-t-octylacrylamide and N-undecylacrylamide.

The vinyl polymers may also result from the homopolymerization or copolymerization of monomers chosen from vinyl esters and styrene monomers. For example, these monomers may be polymerized with acid monomers and/or their esters and/or their amides, such as those mentioned above.

As examples of vinyl esters, there may be mentioned vinyl acetate, vinyl neodecanoate, vinyl pivalate, vinylbenzoate, and vinyl t-butyl benzoate.

As styrene monomers, there may be mentioned styrene and alpha-methylstyrene.

It is possible to use any monomer known to a person skilled in the art entering into the categories of acrylic and vinyl monomers (including the monomers modified by a silicone chain).

Among the polycondensates, there may be mentioned polyurethanes, polyesters, polyester amides, polyamides, and epoxy ester resins and polyureas.

The polyurethanes may be chosen from anionic, cationic, nonionic or amphoteric polyurethanes, polyurethane-acrylics, polyurethane-polyvinyl pyrrolidones, polyester-polyurethanes, polyether-polyurethanes, polyureas, polyurea-polyurethanes, and mixtures thereof.

The polyesters may be obtained, in a known manner, by polycondensation of dicarboxylic acids with polyols, such as diols.

The dicarboxylic acid may be aliphatic, alicyclic or aromatic. There may be mentioned as examples of such acids: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecane-dioic acid, 1,3-cyclohexanedicarboxylic acid, 1,4-cyclohexanedicarboxylic acid, isophthalic acid, terephthalic acid, 2,5-norboranedicarboxylic acid, diglycolic acid, thiodipropionic acid, 2,5-naphthalenedicarboxylic acid and 2,6-naphthalenedicarboxylic acid. These dicarboxylic acid monomers may be used alone or in combination with at least two dicarboxylic acid monomers. Among these monomers, phthalic acid, isophthalic acid and terephthalic acid can be chosen.

The diol may be chosen from aliphatic, alicyclic or aromatic diols. A diol that can be used may be chosen from: ethylene glycol, diethylene glycol, triethylene glycol, 1,3-propanediol, cyclohexanedimethanol and 4-butanediol. As other polyols, there may be used glycerol, pentaerythritol, sorbitol, and trimethylolpropane.

The polyester amides may be obtained in a manner similar to the polyesters, by polycondensation of diacids with diamines or amino alcohols. As diamine, there may be used ethylenediamine, hexamethylenediamine, meta- or para-phenylenediamine. As aminoalcohol, monoethanolamine may be used.

The polyester may, in addition, comprise at least one monomer carrying at least one —$SO_3M$ group, with M representing a hydrogen atom, an ammonium ion $NH_4^+$ or an alkali, alkaline-earth or metal ion, such as for example an $Na^+$, $Li^+$, K+, $Mg^{2+}$, $Ca^{2+}$, $Cu^{2+}$, $Fe^{2+}$ or $Fe^{3+}$ ion. There may also be used, for example, a bifunctional aromatic monomer comprising such an —$SO_3M$ group.

The aromatic ring of the bifunctional aromatic monomer carrying, in addition, an —$SO_3M$ group as described above, may be chosen for example from benzene, naphthalene, anthracene, diphenyl, oxydiphenyl, sulphonyldiphenyl and methylenediphenyl rings. There may also be mentioned as examples of a bifunctional aromatic monomer carrying, in addition, an —$SO_3M$ group: sulphoisophthalic acid, sulphoterephthalic acid, sulphophthalic acid, 4-sulphonaphthalene-2,7-dicarboxylic acid.

The use of copolymers based on isophthalate/sulphoisophthalate, and copolymers obtained by condensation of diethylene glycol, cyclohexanedimethanol, isophthalic acid, and sulphoisophthalic acid may be used. Such polymers are sold, for example, under the trade name Eastman AQ® by the company Eastman Chemical Products.

The optionally modified polymers of natural origin may be chosen from shellac resin, sandarac gum, dammars, elemis, copals, cellulosic polymers and mixtures thereof.

According to one embodiment of the composition according to the invention, the at least one adherent polymer may be present in the form of solid particles in aqueous dispersion, generally known as latex or pseudolatex. The techniques for preparing these dispersions are well known to persons skilled in the art.

As an aqueous dispersion of adherent polymer, there may be used the acrylic dispersions sold under the names NEOCRYL XK-90®, NEOCRYL A-1070®, NEOCRYL A-1090®, NEOCRYL BT-62®, NEOCRYL A-1079®, NEOCRYL A-523® by the company AVECIA-NEORESINS, DOW LATEX 432® by the company DOW CHEMICAL, DAITOSOL 5000 AD® by the company DAITO KASEY KOGYO; or else the aqueous dispersions of polyurethane which are sold under the names NEOREZ R-981®, NEOREZ R-974® by the company AVECIA-NEORESINS, AVALURE UR-405®, AVALURE UR-410®, AVALURE UR-425®, AVALURE UR-450®, SANCURE 875®, SANCURE 861®, SANCURE 878®, SANCURE 2060® by the company GOODRICH, IMPRANIL 85® by the company BAYER, AQUAMERE H-1511® by the company HYDROMER.

As an aqueous dispersion of adherent polymer, there may also be used the dispersions of polymers resulting from the free-radical polymerization of one or more free-radical monomers inside and/or partly at the surface, of preexisting particles of at least one polymer chosen from polyurethanes, polyureas, polyesters, polyesteramides and/or alkyds. These polymers are generally called hybrid polymers.

According to another embodiment of the composition according to the invention, the adherent polymer may be a water-soluble polymer and is therefore present in the aqueous phase of the composition in solubilized form. As examples of water-soluble film-forming polymers there may be mentioned proteins such as proteins of plant origin, such as wheat and soya bean proteins; proteins of animal origin such as keratin, for example keratin hydrolysates and sulphonic keratins;

anionic, cationic, amphoteric and nonionic polymers of chitin and chitosan;

cellulose polymers such as hydroxyethyl cellulose, hydroxypropyl cellulose, methyl cellulose, ethyl hydroxyethyl cellulose, carboxymethyl cellulose, and quaternized derivatives of cellulose;

acrylic polymers and copolymers such as polyacrylates and polymethacrylates;

vinyl polymers, such as polyvinylpyrrolidones, copolymers of methyl vinyl ether and maleic anhydride, the copolymer of vinyl acetate and crotonic acid, copolymers of vinylpyrrolidone and vinyl acetate;

copolymers of vinylpyrrolidone and caprolactam; polyvinyl alcohol;

optionally modified polymers of natural origin, such as:
gum arabic, guar gum, xanthan derivatives, karaya gum;

alginates and carrageenans;

glycoaminoglycans, hyaluronic acid and its derivatives;

shellac resin, sandarac gum, dammars, elemis, copals; deoxyribonucleic acid;

muccopolysaccharides such as hyaluronic acid, chondroitin sulphates, and mixtures thereof.

According to yet another embodiment of the composition according to the invention, the at least one adherent polymer may be present in a liquid fatty phase dispersed in the aqueous phase (aqueous medium) of the composition, the liquid fatty phase comprising oils or organic solvents such as those described above. The expression "liquid fatty phase" is defined herein to mean, in the context of the invention, a fatty phase which is liquid at room temperature (25° C.) and atmospheric pressure (760 mmHg, that is $10^5$ Pa), composed of one or more fatty substances which are liquid at room temperature, also called oils, which are generally compatible with each other.

For instance, the liquid fatty phase can comprise of a volatile oil, optionally in the form of a mixture with a nonvolatile oil, it being possible for the oils to be chosen from the oils cited below.

According to yet another embodiment of the composition according to the invention, the adherent polymer may be present in the form of surface-stabilized particles dispersed in the liquid fatty phase.

The dispersion of surface-stabilized polymer particles may be manufactured as described in the document EP-A-749747, the disclosure of which is incorporated herein by reference.

The polymer particles are surface-stabilized using a stabilizer which may be a block polymer, a graft polymer and/or a random polymer, alone or in the form of a mixture.

Dispersions of film-forming polymer in the liquid fatty phase, in the presence of stabilizing agents, are described in the documents EP-A-749746, EP-A-923928, EP-A-930060, the disclosures of which are incorporated herein by reference.

The size of the polymer particles in dispersion either in the aqueous phase or in the liquid fatty phase may range from 5 nm to 10 μm, such as from 5 nm to 5 μm, and further such as from 5 nm to 600 nm, such as from 20 nm to 300 nm, as measured by methods known to those skilled in the art According to yet another embodiment of the composition according to the invention, the adherent polymer may be solubilized in the liquid fatty phase; the film-forming polymer is then said to be a fat-soluble polymer.

By way of example of a fat-soluble polymer, there may be mentioned copolymers of vinyl ester (the vinyl group being directly linked to the oxygen atom of the ester group and the vinyl ester comprising a linear or branched saturated hydrocarbon radical of 1 to 19 carbon atoms, linked to the carbonyl of the ester group) and of at least one other monomer which may be a vinyl ester (different from the vinyl ester already present), an α-olefin (comprising from 8 to 28 carbon atoms), an alkyl vinyl ether (in which the alkyl group comprises from 2 to 18 carbon atoms), or an allyl or methallyl ester (comprising a linear or branched saturated hydrocarbon radical of 1 to 19 carbon atoms, linked to the carbonyl of the ester group).

These copolymers may be crosslinked using crosslinking agents which may be either of the vinyl type, or of the allyl or methallyl type, such as tetraallyloxyethane, divinylbenzene, divinyl octanedioate, divinyl dodecanedioate, and divinyl octadecanedioate.

As examples of these copolymers, there may be mentioned the copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethyl propionate/vinyl stearate, allyl dimethyl propionate/vinyl stearate, vinyl propionate/vinyl stearate, crosslinked with 0.2% of divinylbenzene, vinyl dimethyl propionate/vinyl laurate, crosslinked with 0.2% of divinylbenzene, vinyl acetate/octadecyl vinyl ether, crosslinked with 0.2% of tetraallyloxyethane, vinyl acetate/allyl stearate, crosslinked with 0.2% of divinylbenzene, vinyl acetate/1-octadecene crosslinked with 0.2% of divinylbenzene and allyl propionate/allyl stearate crosslinked with 0.2% of divinylbenzene.

As fat-soluble polymers, there may also be mentioned fat-soluble homopolymers, and, for example, those resulting from the homopolymerization of vinyl esters comprising from 9 to 22 carbon atoms or of alkyl acrylates or methacrylates, the alkyl radicals comprising from 10 to 20 carbon atoms.

Such fat-soluble homopolymers may be chosen from polyvinyl stearate, polyvinyl stearate crosslinked using divinylbenzene, diallyl ether or diallyl phthalate, polystearyl (meth)acrylate, polyvinyl laurate, polylauryl (meth)acrylate, it being possible for these poly(meth)acrylates to be crosslinked using ethylene glycol or tetraethylene glycol dimethacrylate.

The fat-soluble copolymers and homopolymers defined above are known and are described in application FR-A-2232303 (the disclosure of which is incorporated herein by reference); they may have a weight-average molecular weight ranging from 2,000 to 500,000, such as from 4,000 to 200,000.

As film-forming fat-soluble polymers which can be used in the invention, there may also be mentioned polyalkylenes and copolymers of $C_2$–$C_{20}$ alkenes, such as polybutene, alkyl celluloses with a saturated or unsaturated, linear or branched, $C_1$ to $C_8$ alkyl radical such as ethyl cellulose and propyl cellulose, copolymers of vinylpyrrolidone (VP) and copolymers of vinylpyrrolidone and of a $C_2$ to $C_{40}$ alkene, such as of a $C_3$ to $C_{20}$ alkene. By way of example of a VP copolymer which can be used in the invention, there may be mentioned the VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene and VP/acrylic acid/lauryl methacrylate copolymer.

The composition according to the invention may comprise a film-forming aid which promotes the formation of a film with the film-forming polymer. Such a film-forming agent may be chosen from all the compounds known to persons skilled in the art to be capable of fulfilling the desired function, and may be chosen from plasticizing agents and coalescing agents.

According to an embodiment of the composition according to the invention, the adherent polymer may be a polymer capable of forming a deposit, such as a film, producing, at a concentration of 7% in water, a retraction of isolated stratum corneum of more than 1% at 30° C. under a relative humidity of 40%, for instance of more than 1.2%, such as more than 1.5%. This retraction is measured using an extensiometer, according to the method described below.

The volatile solvent present in the composition may be chosen from water or volatile organic compounds, or mixtures thereof.

The composition according to the invention may comprise, in addition, at least one additional wax different from the wax of the second secondary solid particles described above.

As additional wax, there may be mentioned beeswax, lanolin wax, Chinese wax, rice wax, Carnauba wax, certain microcrystalline waxes, paraffin waxes, certain ozokerites, certain polyethylene waxes, certain waxes obtained by Fisher-Tropsch synthesis. There may also be mentioned the waxes obtained by catalytic hydrogenation of animal or vegetable oils having linear or branched $C_8$–$C_{32}$ fatty chains. Among these, there may be mentioned, for example, hydrogenated sunflower oil, hydrogenated castor oil, hydrogenated copra oil and hydrogenated lanolin oil. Silicon waxes or fluorinated waxes may also be mentioned.

The additional waxes present in the composition may be dispersed in the form of particles in the aqueous medium of the composition. These particles may have a mean size ranging from 50 nm to 50 µm, such as from 50 nm to 10 µm, as measured by methods known to those skilled in the art.

For example, the additional waxes can be present in the composition according to the invention in the form of solid particles and therefore form part of the second solid particles defined above.

The additional wax may be present in the composition according to the invention in an amount ranging from 0.1% to 50% by weight, relative to the total weight of the composition, such as from 0.5% to 30% by weight, and further such as from 1% to 20% by weight.

According to one embodiment of the composition according to the invention, the composition may comprise an aqueous medium, constituting an aqueous phase, which may be the continuous phase of the composition.

The aqueous phase may comprise, or even essentially comprise, water; it may also comprise a mixture of water and a water-miscible organic solvent (solvent capable of forming with water a homogeneous mixture transparent to the eye at 25° C.) such as lower monoalcohols having from 1 to 5 carbon atoms such as ethanol, isopropanol, glycols having from 2 to 8 carbon atoms such as propylene glycol, ethylene glycol, 1,3-butylene glycol, dipropylene glycol, $C_3$–$C_4$ ketones, $C_2$–$C_4$ aldehydes.

The aqueous phase (water and optionally the water-miscible organic solvent) may be present in an amount ranging from 1% to 95% by weight, relative to the total weight of the composition, such as from 3% to 80% by weight, and further such as from 5% to 60% by weight.

According to another embodiment of the composition according to the invention, the composition may comprise at least one volatile organic solvent or oil which may form a fatty phase or a continuous fatty phase. The composition may be an anhydrous composition.

The expression "volatile organic solvent or oil" is defined herein to mean, in the context of the invention, volatile cosmetic oils and organic solvents, which are liquid at room temperature, having a non-zero vapour pressure, at room temperature and atmospheric pressure, ranging from $10^{-2}$ to 300 mmHg (1.33 Pa to 40 000 Pa), for example, greater than 0.3 mmHg (40 Pa). The expression "nonvolatile oil" is defined herein to mean an oil having a vapour pressure of less than $10^{-2}$ mmHg (1.33 Pa) at room temperature and atmospheric pressure.

These oils may be hydrocarbon oils, silicone oils, fluorinated oils, or mixtures thereof.

The expression "hydrocarbon oil" is defined herein to mean an oil comprising mainly hydrogen and carbon atoms and optionally oxygen, nitrogen, sulphur and phosphorus atoms. The volatile hydrocarbon oils may be chosen from hydrocarbon oils comprising from 8 to 16 carbon atoms, branched $C_8$–$C_{16}$ alkanes such as $C_8$–$C_{16}$ isoalkanes of petroleum origin (also called isoparaffins) such as isododecane (also called 2,2,4,4,6-pentamethylheptane), isodecane, isohexadecane, and for example the oils sold under the trade names Isopars' or Permetyls, $C_8$–$C_{16}$ branched esters, isohexyl neopentanoate, and mixtures thereof. Other volatile hydrocarbon oils such as petroleum distillates, such as those sold under the name Shell Solt by the company SHELL, may also be used. For example, the volatile solvent is chosen from volatile hydrocarbon oils comprising from 8 to 16 carbon atoms and mixtures thereof.

As volatile oils, there may also be used volatile silicones, such as for example volatile linear or cyclic silicone oils, such as those having a viscosity $\leq 8$ centistokes ($8 \times 10^{-6}$ m²/s), and comprising from 2 to 7 silicon atoms, these silicones optionally comprising alkyl or alkoxy groups having from 1 to 10 carbon atoms. As volatile silicone oil which can be used in the invention, there may be mentioned octamethylcyclotetrasiloxane, decamethylcyclopentasiloxane, dodecamethylcyclohexasiloxane, heptamethylhexyltrisiloxane, heptamethyl-octyltrisiloxane, hexamethyldisiloxane, octamethyltri-siloxane, decamethyltetrasiloxane, dodecamethylpenta-siloxane, and mixtures thereof.

The volatile oil may be present in the composition according to the invention in an amount ranging from 0.1% to 98% by weight, relative to the total weight of the composition, such as from 1% to 65% by weight.

The composition may also comprise at least one nonvolatile oil chosen from nonvolatile hydrocarbon and/or silicone and/or fluorinated oils.

As nonvolatile hydrocarbon oil, there may be mentioned:
hydrocarbon oils of plant origin such as triglycerides comprising of esters of fatty acids and of glycerol in which the fatty acids may have varying chain lengths from $C_4$ to $C_{24}$, it being possible for the latter to be linear or branched, saturated or unsaturated; these oils can be chosen from wheatgerm oil, sunflower oil, grapeseed oil, sesame oil, maize oil, apricot oil, castor oil, karite oil, avocado oil, olive oil, soyabean oil, sweet almond oil, palm oil, rapeseed oil, cottonseed oil, hazelnut oil, macadamia oil, jojoba oil, lucerne oil, poppyseed oil, pumpkinseed oil, sesame oil, gourd oil, rapeseed oil, blackcurrant seed oil, evening primrose oil, millet oil, barley oil, quinoa oil, rye oil, safflower oil, candlenut oil, passionflower oil, rose-muscat oil; and triglycerides of caprylic/capric acids such as those sold by the company Stéarineries Dubois and those sold under the names Miglyol 810, 812 and 818 by the company Dynamit Nobel, synthetic ethers comprising from 10 to 40 carbon atoms;

linear or branched hydrocarbons of mineral or synthetic origin such as petroleum jelly, polydecenes, hydrogenated polyisobutene such as parleam, squalane, and mixtures thereof;

synthetic esters such as the oils of formula $R_1COOR_2$ in which $R_1$ represents the residue of a linear or branched fatty acid comprising from 1 to 40 carbon atoms and $R_2$ represents a hydrocarbon chain, a branched hydrocarbon chain, comprising from 1 to 40 carbon atoms provided that $R_1+R_2$ is $\geq 10$, such as for example Purcellin oil (ketostearyl octanoate), isopropyl myristate, isopropyl palmitate, $C_{12}$ to $C_{15}$ alcohol benzoate, hexyl laurate, diisopropyl adipate, isononyl isononanoate, 2-ethylhexyl palmitate, isostearates, octanoates, decanoates or ricinoleates of alcohols or of polyalcohols such as propylene glycol dioctanoate; hydroxylated esters such as isostearyl lactate, diisostearyl malate; and esters of pentaerythritol;

fatty alcohols which are liquid at room temperature comprising a branched and/or unsaturated carbon chain having from 12 to 26 carbon atoms such as octyl dodecanol, isostearyl alcohol, oleyl alcohol, 2-hexyldecanol, 2-butyloctanol, 2-undecylpentadecanol;

higher fatty acids such as oleic acid, linoleic acid, linolenic acid; and mixtures thereof.

The nonvolatile silicone oils which can be used in the composition according to the invention may be nonvolatile polydimethylsiloxanes (PDMS), polydimethylsiloxanes comprising alkyl or alkoxy groups, pendant and/or at the silicone chain end, groups each comprising from 2 to 24 carbon atoms, phenylated silicones such as phenyltrimethicones, phenyldimethicones, phenyltrimethylsiloxydi-phenylsiloxanes, diphenyldimethicones, diphenylmethyl-diphenyltrisiloxanes, and (2-phenylethyl)trimethylsioloxysilicates.

The fluorinated oils which can be used in the invention are in particular fluorosilicone oils, fluorinated polyethers, fluorinated silicones as described in the document EP-A-847752, the disclosure of which is incorporated herein by reference.

The nonvolatile oils may be present in the composition according to the invention in an amount ranging from 0.1% to 50% by weight, such as from 0.1% to 30% by weight, relative to the total weight of the composition, and further such as from 0.1% to 20% by weight.

The composition according to the invention may contain emulsifying surfactants present in a proportion ranging from 2 to 30% by weight relative to the total weight of the composition, such as from 5% to 15%. These surfactants may be chosen from anionic or nonanionic surfactants. Reference may be made to the document "Encyclopedia of Chemical Technology, KIRK-OTHMER", volume 22, p. 333–432, $3^{rd}$ edition, 1979, WILEY (the disclosure of which is incorporated by reference), for the definition of the properties and functions (emulsifier) of the surfactants, such as discussed at p. 347–377 of this reference, for anionic and nonionic surfactants.

The surfactants which may be used in the composition according to the invention are chosen:
from nonionic surfactants: fatty acids, fatty alcohols, polyethoxylated and polyglycerolated fatty alcohols such as polyethoxylated stearyl and cetylstearyl alcohols, esters of fatty acid and of sucrose, esters of alkyl glucose, in particular polyoxyethylenated fatty esters of $C_1$–$C_6$ alkyl glucose, and mixtures thereof;
from anionic surfactants: $C_{16}$–$C_{30}$ fatty acids neutralized with amines, aqueous ammonia or alkaline salts and mixtures thereof; oxyethylenated acrylic acid/monostearyl itaconate copolymer (20 EO) as an aqueous dispersion at 30% by weight sold under the name "STRUCTURE 2001" by the company National Starch, ethoxylated acrylic acid/monocetyl itaconate copolymer (20 EO) as an aqueous dispersion at 30% sold under the name "STRUCTURE 3001" by the company National Starch.

Surfactants which allow the production of an oil-in-water or wax-in-water emulsion can be used.

The composition according to the invention may also comprise a colouring substance such as pulverulent colouring substances, fat-soluble colorants, water-soluble colorants. This colouring substance may be present in an amount ranging from 0.01% to 50% by weight, relative to the total weight of the composition, such as ranging from 0.01% to 30% by weight.

The pulverulent colouring substances may be chosen from pigments and pearlescent agents.

The pigments may be white or coloured, inorganic and/or organic, coated or otherwise. There may be mentioned, among the inorganic pigments, titanium dioxide, optionally surface-treated, zirconium, zinc or cerium oxides, as well as iron or chromium oxides, manganese violet, ultramarine blue, chromium hydrate and ferric blue. Among the organic pigments, there may be mentioned carbon black, pigments of the D & C type, and lacquers based on carmine, barium, strontium, calcium or aluminium.

The pearlescent agents may be chosen from white pearlescent pigments such as mica coated with titanium or bismuth oxychloride, coloured pearlescent pigments such as mica-titanium with iron oxides, mica-titanium with ferric blue or chromium oxide, mica-titanium with an organic pigment of the abovementioned type as well as pearlescent pigments based on bismuth oxychloride.

The fat-soluble colorants can be, for example, Sudan red, D&C Red 17, D&C Green 6, β-carotene, soyabean oil, Sudan brown, D&C Yellow 11, D&C Violet 2, D&C Orange 5, quinoline yellow, annatto. The water-soluble colorants can be, for example, sugarbeet juice and methylene blue.

The composition of the invention may comprise, in addition, any additive conventionally used in cosmetics, such as antioxidants, fillers, preservatives, perfumes, neutralizing agents, thickeners, cosmetic or dermatological active agents such as, for example, emollients, coalescing agents, plasticizing agents, moisturizers, vitamins, sunscreens, and mixtures thereof. These additives may be present in the composition in an amount ranging from 0.01 to 20% of the total weight of the composition such as from 0.01 to 10% (if present).

The composition according to the invention may be provided in the form of an oil-in-water emulsion, a water-in-oil emulsion, a wax-in-water dispersion or alternatively may be an anhydrous composition.

Of course persons skilled in the art will be careful to choose the possible additional additives and/or their quantity such that the advantageous properties of the composition according to the invention are not or not substantially impaired by the addition envisaged.

The composition according to the invention may be manufactured by known methods which are generally used in the cosmetic or dermatological field.

Method of Measuring the Density of Solid Particles:

The apparent density of solid particles is measured using a Gay-Lussac pycnometer.

A precision scale (precision of 1 mg) is used and the measurements are carried out in a thermostatic chamber at 25° C. (±0.5° C.). Two reference liquids having a density d, which are demineralized water (d=1000 kg/m$^3$) and heptane (d=683.7 kg/m$^3$) are also used. The density of the solid particles is measured with each reference liquid.

The pycnometer and the products used for carrying out the measurement are placed at the temperature of 25° C. The masses cited below are expressed in kilograms.

The mass M0 of the pycnometer is measured, then the pycnometer is completely filled with the reference liquid used, avoiding introducing air bubbles. The mass M1 of the filled pycnometer is measured.

A mixture of mass M2 of the material whose density d2 it is desired to measure with a mass M3 of reference liquid is then prepared. The mixture is stirred and then just before the end of stirring, the pycnometer is filled with this mixture and the mass M4 of the filled pycnometer is measured. The mass M4−M0 of the mixture present in the pycnometer is thus measured.

The pycnometer having a constant filling volume, it is therefore possible to establish the following relationship: (M1−M0)/d=(M2/d2+M3/d)×(M4−M0)/(M2+M3)

This relationship makes it possible to calculate the value of the density d2 of the solid particles, expressed in kg/m$^3$. A value of the density of the solid particles is thus determined for each of the reference liquids. According to the invention, the highest value (among the density measured with distilled water and the density measured with heptane) is selected as value of the density for the determination of the volume fraction of the solid particles.

Method for Measuring Retraction of a Polymer:

The principle consists in measuring, before treatment and after treatment, the length of a test piece of isolated stratum corneum and determining the percentage retraction of the test piece.

Test pieces of 1 cm×0.4 cm of stratum corneum are used which have a thickness ranging from 10 to 20 µm placed on the extensiometer MTT 610 marketed by the company DIASTRON.

The test piece is placed between 2 jaws and left for 12 hours in an atmosphere at 30° C. and 40% relative humidity.

The test piece is drawn, at the rate of 2 mm/minute, by a length of between 5 and 10% of the initial length in order to determine the length $I_1$ from which the test piece begins to exert a force on the jaws and which is detected by the apparatus.

The test piece is then relaxed and then 2 mg of an aqueous composition containing 7% by weight of polymer are applied to the stratum corneum. After complete evaporation of the composition, the test piece is drawn under the same conditions as those described above in order to also determine the length $I_2$ for the treated test piece.

The percentage retraction is determined by the ratio: $100 \times (I_2 - I_1)/I_1$.

The invention is illustrated in greater detail in the following non-limiting example.

EXAMPLE 1

A mascara having the following composition is prepared:

| | |
|---|---|
| Styrene acrylic copolymer as a 30% aqueous dispersion of polymer (Joncryl SCX 8082 from Johnson Polymers)* | 25 g AS |
| Black iron oxide (Sicovit black 85E172 from BASF | 5 g |
| Hydroxyethylcellulose (Cellosize QP4400M from Amerchol) | 1 g |
| Propylene glycol | 5 g |
| Water | qs 100 g |

*latex having a glass transition temperature Tg = 102° C.

A mascara is obtained whose nonvolatile fraction (formed of all the constituents except water) contains a volume fraction of solid particles (styrene/acrylic copolymer, black iron oxide) equal to 81% (relative to the total volume of the nonvolatile fraction); the volume fraction of the first particles for the purposes of the present invention (styrene/acrylic copolymer) represents 96.1% of the total volume of the solid particles.

The eyelashes to which this mascara has been applied as make-up exhibit good curling.

What is claimed is:

1. A composition for coating keratinous fibres comprising, in a cosmetically acceptable medium, at least one volatile solvent and a nonvolatile fraction comprising:
   at least one polymer capable of adhering to the keratinous fibres,
   first solid particles comprising a first at least one amorphous material which is solid at 25° C. and exhibits a glass transition temperature greater than or equal to 60° C.,
   and optionally second solid particles comprising a second material, different from the first material, said second solid particles not being capable of coalescing at a temperature of less than or equal to 40° C.;
   wherein the first and, where appropriate, the second solid particles are present in the composition in an amount such that the volume fraction of the first solid particles and, where appropriate, of the second solid particles is greater than or equal to 50% of the total volume of the nonvolatile fraction of the composition, and the volume fraction of the first solid particles is greater than or equal to 30% of the total volume fraction of the first and second solid particles, and
   wherein the keratinous fibers are chosen from natural eyelashes, false eyelashes, hair, and wigs.

2. The composition according to claim 1, wherein the first at least one amorphous material has a glass transition temperature greater than or equal to 80° C.

3. The composition according to claim 1, wherein the first at least one amorphous material has a glass transition temperature greater than or equal to 100° C.

4. The composition according to claim 1, wherein the first at least one amorphous material is chosen from polymers.

5. The composition according to claim 1, wherein the first at least one amorphous material is chosen from polymers chosen from free-radical polymers and polycondensates.

6. The composition according to claim 1, wherein the first at least one amorphous material is chosen from polymers chosen from ethylene polymers, propylene polymers, acrylic polymers, acrylamide polymers, (meth)acrylonitrile polymers, polycarbonates, polyurethanes, polyesters, polyamides, polysulphones, polysulphonamides, and carbohydrates.

7. The composition according to claim 1, wherein the first solid particles have a mean size ranging from 10 nm to 50 µm.

8. The composition according to claim 7, wherein the first solid particles have a mean size ranging from 20 nm to 1 µm.

9. The composition according to claim 1, wherein the composition comprises the first solid particles and the second solid particles.

10. The composition according to claim 1, wherein the volume fraction of the first solid particles and, where appropriate, of the second solid particles ranges from 50% to 99% of the total volume of the nonvolatile fraction of the composition.

11. The composition according to claim 1, wherein the volume fraction of the first solid particles and, where appropriate, of the second solid particles is greater than or equal to 60% of the total volume of the nonvolatile fraction of the composition.

12. The composition according to claim 11, wherein the volume fraction of the first solid particles and, where appropriate, of the second solid particles ranges from 60% to 99% of the total volume of the nonvolatile fraction of the composition.

13. The composition according to claim 1, wherein the volume fraction of the first solid particles and, where appropriate, of the second solid particles is greater than or equal 70% of the total volume of the nonvolatile fraction of the composition.

14. The composition according to claim 13, wherein the volume fraction of the first solid particles and, where appropriate, of the second solid particles ranges from 70% to 95% of the total volume of the non-volatile fraction of the composition.

15. The composition according to claim 1, wherein the second solid particles are chosen from:
   second primary solid particles, comprising at least one material chosen from crystalline and semicrystalline materials which are solid at 25° C. and exhibit at least one of a first order phase transition, a melting transition, and a combustion transition greater than 100° C.,
second secondary solid particles comprising at least one wax having a hardness of greater than 6.5 MPa,
second tertiary solid particles different from said second primary and said second secondary particles,
and mixtures thereof.

16. The composition according to claim 1, wherein the second solid particles comprise second primary solid particles comprising at least one material chosen from crystalline and semicrystalline materials which are solid at 25° C. and exhibit at least one of a first order phase transition, a melting transition, and a combustion transition greater than 100° C.

17. The composition according to claim 15, wherein the at least one material has a first order phase transition greater than 120° C.

18. The composition according to claim 17, wherein the crystalline or semicrystalline material has a first order phase transition greater than 150° C.

19. The composition according to claim 15, wherein the at least one material has a Vicker hardness greater than or equal to 10.

20. The composition according to claim 19, wherein the at least one material has a Vicker hardness ranging from 10 to 7,500.

21. The composition according to claim 15, wherein the at least one material has a Vicker hardness greater than or equal to 200.

22. The composition according to claim 21, wherein the at least one material has a Victor hardness ranging from 200 to 7,500.

23. The composition according to claim 15, wherein the at least one material has a Vicker hardness greater than or equal to 400.

24. The composition according to claim 23, wherein the at least one material has a Vicker hardness ranging from 400 to 7,500.

25. The composition according to claim 15, wherein the at least one material is chosen from silica, glass, diamond, copper, boron nitride, ceramics, metal oxides, and polyamides.

26. The composition according to claim 25, wherein said metal oxides are chosen from iron oxides.

27. The composition according to claim 15, wherein the second primary solid particles have a mean size ranging from 5 nm to 50 μm.

28. The composition according to claim 27, wherein the second primary solid particles have a mean size ranging from 20 nm to 50 μm.

29. The composition according to claim 1, wherein the composition further comprises second secondary particles comprising at least one wax having a hardness greater than or equal to 6.5 MPa.

30. The composition according to claim 29, wherein the at least one wax has a melting point ranging from 30° C. to 99° C.

31. The composition according to claim 30, wherein the at least one wax has a melting point ranging from 40° C. to 99° C.

32. The composition according to claim 29, wherein the at least one wax has a melting point greater than or equal to 30° C. and less than 77° C.

33. The composition according to claim 32, wherein the at least one wax has a melting point greater than or equal to 30° C. and less than 60° C.

34. The composition according to claims 29, wherein the at least one wax has a hardness ranging from 6.5 MPa to 20 MPa.

35. The composition according to claim 34, wherein the at least one wax has a hardness ranging from 9.7 MPa to 20 MPa.

36. The composition according to claim 35, wherein the at least one wax has a hardness ranging from 10 MPa to 12 MPa.

37. The composition according to claim 29, wherein the at least one wax has a hardness ranging from 10 to 20 MPa.

38. The composition according to claim 29, wherein the at least one wax is chosen from Candelilla wax, hydrogenated jojoba wax, sumac wax, ceresin, octacosanyl stearate, tetracontanyl stearate, Shellac wax, behenyl fumarate, di(1,1-trimethylolpropane) tetrastearate, di(1,1,1-trimethylolpropane) tetrabehenate, ozokerites, the wax obtained by hydrogenation of olive oil esterified with stearyl alcohol, and waxes obtained by hydrogenation of castor oil esterified with cetyl alcohol.

39. The composition according to claim 29, wherein the at least one wax is chosen from di(1,1,1-trimethylolpropane) tetrastearate and the olive wax obtained by hydrogenation of olive oil esterified with stearyl alcohol.

40. The composition according to claim 29, wherein the second secondary solid particles have a mean size ranging from 50 nm to 50 μm.

41. The composition according to claim 40, wherein the second secondary solid particles have a mean size ranging from 50 nm to 10 μm.

42. The composition according to claim 1, wherein the second solid particles comprise second tertiary solid particles.

43. The composition according to claim 1, wherein the volume fraction of the first solid particles ranges from 30% to 100% of the total volume fraction of the first and second solid particles.

44. The composition according to claim 1, wherein the volume fraction of the first solid particles and of the second primary solid particles is greater than or equal to 10.05% of the total volume of the first and second solid particles.

45. The composition according to claim 44, wherein the volume fraction of the first solid particles and of the second primary solid particles is greater than or equal to 20.05% of the total volume of the first and second solid particles.

46. The composition according to claim 45, wherein the volume fraction of the first solid particles and of the second primary solid particles is greater than or equal to 30.05% of the total volume of the first and second solid particles.

47. The composition according to claim 46, wherein the volume fraction of the first solid particles and of the second primary solid particles is greater than or equal to 40.05% of the total volume of the first and second solid particles.

48. The composition according to claim 47, wherein the volume fraction of the first solid particles and of the second primary solid particles is greater than or equal to 50.05% of the total volume of the first and second solid particles.

49. The composition according to claim 1, wherein at least one volatile solvent is chosen from water, volatile organic solvents, and volatile oils.

50. The composition according to claim 1, wherein the at least one polymer capable of adhering to said keratinous fibres is chosen from vinyl polymers, polyurethanes, polyesters, polyamides, polyureas, and cellulose polymers.

51. The composition according to claim 1, wherein the at least one polymer capable of adhering to said keratinous fibres is chosen from film-forming polymers at a temperature of less than or equal to 40° C.

52. The composition according to claim 1, wherein the at least one polymer capable of adhering to a keratinous materials is a polymer capable of forming a deposit producing, at a concentration of 7% in water, a retraction of the isolated stratum corneum of more than 1% at 30° C. at a relative humidity of 40%.

53. The composition according to claim 52, wherein the retraction of the stratum corneum is of more than 1.2%.

54. The composition according to claim 53, wherein the retraction of the stratum corneum is of more than 1.5%.

55. The composition according to claim 1, wherein the at least one polymer capable of adhering to a keratinous material is present in an amount ranging from 0.1% to 50% by weight, relative to the total weight of the composition.

56. The composition according to claim 55, wherein the at least one polymer capable of adhering to a keratinous material is present in an amount ranging from 0.5% to 40% by weight, relative to the total weight of the composition.

57. The composition according to claim 56, wherein the at least one polymer capable of adhering to a keratinous material is present in an amount ranging from 1% to 30% by weight, relative to the total weight of the composition.

58. The composition according to claim 1, wherein the composition further comprises an aqueous phase.

59. The composition according to claim 1, wherein the composition further comprises an aqueous phase chosen from water and a mixture of water and water-miscible organic solvent.

60. The composition according to claim 59, wherein the water-miscible organic solvent is chosen from lower monoalcohols having from 1 to 5 carbon atoms, glycols having from 2 to 8 carbon atoms, $C_3$–$C_4$ ketones, and $C_2$–$C_4$ aldehydes.

61. The composition according to claim 59, wherein the aqueous phase is present in an amount ranging from 1% to 95% by weight, relative to the total weight of the composition.

62. The composition according to claim 61, wherein the aqueous phase is present in an amount ranging from 3% to 80% by weight, relative to the total weight of the composition.

63. The composition according to claim 62, wherein the aqueous phase is present in an amount ranging from 5% to 60% by weight, relative to the total weight of the composition.

64. The composition according to claim 59, wherein the at least one polymer capable of adhering to a keratinous material is solubilized in the aqueous phase.

65. The composition according to claim 59, wherein the at least one polymer capable of adhering to a keratinous material is in the form of solid particles in aqueous dispersion.

66. The composition according to any claim 1, wherein the composition further comprises at least one volatile oil.

67. The composition according to claim 66, wherein at least one volatile oil is chosen from hydrocarbon oils, silicone oils, and fluorinated oils.

68. The composition according to claim 66, wherein the at least one volatile oil is present in an amount ranging from 0.1% to 98% by weight, relative to the total weight of the composition.

69. The composition according to claim 66, wherein the at least one volatile oil is present in an amount ranging from 1% to 65% by weight, relative to the total weight of the composition.

70. The composition according to claim 1, wherein the composition further comprises at least one nonvolatile oil.

71. The composition according to claim 70, wherein the at least one nonvolatile oil is present in an amount ranging from 0.1% to 50% by weight relative to the total weight of the composition.

72. The composition according to claim 71, wherein the at least one nonvolatile oil is present in an amount ranging from 0.1% to 30% by weight, relative to the total weight of the composition.

73. The composition according to claim 72, wherein the at least one nonvolatile oil is present in an amount ranging from 0.1% to 20% by weight, relative to the total weight of the composition.

74. The composition according to claim 1, wherein the at least one polymer capable of adhering to a keratinous material is solubilized or dispersed in the form of surface-stabilized particles in a liquid fatty phase.

75. The composition according to claim 15, wherein the composition further comprises an additional wax different from the wax of the second secondary solid particles.

76. The composition according to claim 75, wherein the additional wax is present in the composition in an amount ranging from 0.1% to 50% by weight, relative to the total weight of the composition.

77. The composition according to claim 76, wherein the additional wax is present in the composition in an amount ranging from 0.5% to 30% by weight, relative to the total weight of the composition.

78. The composition according to claim 77, wherein the additional wax is present in the composition in an amount ranging from 1% to 20% by weight, relative to the total weight of the composition.

79. The composition according to claim 75, wherein the additional wax is in the form of particles having a mean size ranging from 50 nm to 50 µm.

80. The composition according to claim 79, wherein the additional wax is in the form of particles having a mean size ranging from 50 nm to 10 µm.

81. The composition according to claim 1, wherein the composition further comprises a surfactant.

82. The composition according to claim 1, wherein the composition further comprises at least one additive chosen from colouring substances, antioxidants, fillers, preservatives, perfumes, neutralizing agents, thickeners, cosmetic active agents, sunscreens, coalescing agents, and plasticizers.

83. The composition according to claim 1, wherein the composition is a mascara.

84. A method for applying make-up to or a nontherapeutic treatment of keratinous fibres comprising applying to said keratinous fiber a composition comprising, in a cosmetically acceptable medium, at least one volatile solvent and a nonvolatile fraction comprising:

at least one polymer capable of adhering to said keratinous fibres;

first solid particles comprising a first at least one amorphous material which is solid at 25° C. and exhibits a glass transition temperature greater than or equal to 60° C.;

and optionally second solid particles comprising a second material, different from the first material, said second solid particles not being capable of coalescing at a temperature of less than or equal to 40° C.;

wherein the first and, where appropriate, the second solid particles are present in the composition in an amount such that the volume fraction of the first solid particles and, where appropriate, of the second solid particles is greater than or equal to 50% of the total volume of the nonvolatile fraction of the composition, and the volume fraction of the first solid particles is greater than or equal to 30% of the total volume fraction of the first and second solid particles.

85. The method or treatment according to claim 84, wherein said keratinous fibres are eyelashes.

86. A method for curling keratinous fibres comprising applying to said keratinous fibres a composition comprising, in a cosmetically acceptable medium, at least one volatile solvent and a nonvolatile fraction comprising:
   at least one polymer capable of adhering to said keratinous fibres;
   first solid particles comprising a first at least one amorphous material which is solid at 25° C. and exhibits a glass transition temperature greater than or equal to 60° C.;
   and optionally second solid particles comprising a second material, different from the first material, said second solid particles not being capable of coalescing at a temperature of less than or equal to 40° C.;
      wherein the first and, where appropriate, the second solid particles are present in the composition in an amount such that the volume fraction of the first solid particles and, where appropriate, of the second solid particles is greater than or equal to 50% of the total volume of the nonvolatile fraction of the composition, and the volume fraction of the first solid particles is greater than or equal to 30% of the total volume fraction of the first and second solid particles.

87. The method according to claim 86, wherein said keratinous fibres are eyelashes.

88. A method for curling keratinous fibres comprising applying to said keratinous fibres a mascara comprising, in a cosmetically acceptable medium:
   first solid particles of a first at least one amorphous material which is solid at 25° C. and has a glass transition temperature greater than 60° C.;
   optionally second solid particles of a second material, different from said first material, said second solid particles not being capable of coalescing at a temperature of less than or equal to 40° C.;
   at least one volatile solvent; and
   a nonvolatile fraction comprising at least one polymer capable of adhering to said keratinous fibres
      wherein the first solid particles and, where appropriate, the second solid particles are present in the composition in an amount such that the volume fraction of the first solid particles and, where appropriate, of the second solid particles is greater than or equal 50% of the total volume of the nonvolatile fraction of the composition, and the volume fraction of the first solid particles is greater than or equal to 30% of the total volume fraction of the first and second solid particles.

89. The method according to claim 88, wherein the keratinous fibres are eyelashes.

90. A composition for coating keratinous fibres comprising, in a cosmetically acceptable medium, at least one volatile solvent and a nonvolatile fraction comprising:
   first solid particles comprising a first at least one amorphous material which is solid at 25° C. and exhibits a glass transition temperature greater than or equal to 60° C.,
   and optionally second solid particles comprising a second material, different from the first material, said second solid particles not being capable of coalescing at a temperature of less than or equal to 40° C.;
wherein the first and, where appropriate, the second solid particles are present in the composition in an amount such that the volume fraction of the first solid particles and, where appropriate, of the second solid particles is greater than or equal to 50% of the total volume of the nonvolatile fraction of the composition, wherein at least a portion of at least one of said first solid particles and said optional second solid particles comprises at least one polymer capable of adhering to said keratinous fibres, and the volume fraction of the first solid particles is greater than or equal to 30% of the total volume fraction of the first and second solid particles, and
   wherein the keratinous fibers are chosen from natural eyelashes, false eyelashes, hair, and wigs.

* * * * *

UNITED STATES PATENT AND TRADEMARK OFFICE
CERTIFICATE OF CORRECTION

PATENT NO. : 7,138,110 B2
APPLICATION NO. : 10/195428
DATED : November 21, 2006
INVENTOR(S) : Auguste et al.

Page 1 of 1

It is certified that error appears in the above-identified patent and that said Letters Patent is hereby corrected as shown below:

Column 18, lines 56-57, "equal 70%" should read --equal to 70%--.

Column 20, line 1, "claims" should read --claim--.

Column 21, line 5, "materials" should read --material--.

Column 21, line 55, "to any claim" should read --to claim--.

Column 24, line 9, "equal 50%" should read --equal to 50%--.

Signed and Sealed this

Thirteenth Day of February, 2007

JON W. DUDAS
*Director of the United States Patent and Trademark Office*